United States Patent [19]
Maurer

[11] 4,340,063
[45] Jul. 20, 1982

[54] STIMULATION DEVICE
[75] Inventor: Donald D. Maurer, Anoka, Minn.
[73] Assignee: EMPI, Inc., Fridley, Minn.
[21] Appl. No.: 121,395
[22] Filed: Feb. 14, 1980

Related U.S. Application Data
[63] Continuation-in-part of Ser. No. 109,175, Jan. 2, 1980, abandoned.

[51] Int. Cl.³ ............................................. A61N 1/36
[52] U.S. Cl. .................................................. 128/421
[58] Field of Search ................... 128/419 R, 421, 422

[56] References Cited

U.S. PATENT DOCUMENTS

| | | | |
|---|---|---|---|
| 2,808,826 | 10/1957 | Reiner et al. | 128/422 |
| 3,077,884 | 2/1963 | Batrow et al. | 128/423 |
| 3,127,895 | 4/1964 | Kendall et al. | 128/422 |
| 3,646,940 | 3/1972 | Timm et al. | 128/421 |
| 3,817,252 | 6/1974 | Maurer | 128/798 |
| 3,817,254 | 6/1974 | Maurer | 128/421 |
| 3,888,261 | 6/1975 | Maurer | 128/420 R |
| 4,014,347 | 3/1977 | Halleck et al. | 128/422 |
| 4,210,151 | 7/1980 | Keller, Jr. | 128/421 |

*Primary Examiner*—William E. Kamm
*Attorney, Agent, or Firm*—L. Paul Burd; Richard O. Bartz; Robert W. Gutenkauf

[57] ABSTRACT

A device operable to electrically stimulate living tissue, including body organs, muscles and nerves. The device can be applied to the surface of the body or implanted in the body. The device has an electrical circuit containing a pulse width control for variation of the stimulus intensity, pulse repetition rate, and on-time of the pulse to vary the pulse width. A variation in pulse width causes the stimulus variation of the stimulus intensity in a prescribed mathematical manner so as to approximately follow the curves of the strength-duration pulse stimulus amplitude versus pulse width. This provides for an optimal selection among the various classes of stimulated nerve fibers within a nerve tract or bundle. A precise adjustment of stimulation can be achieved so as to optimize sensation of pain relief.

23 Claims, 3 Drawing Figures

STIMULATION DEVICE

CROSS REFERENCE TO RELATED APPLICATION

This application is a continuation-in-part of U.S. application Ser. No. 109,175, filed Jan. 2, 1980, now abandoned.

BACKGROUND OF INVENTION

It is known that patient pain can be alleviated by the application of electrical pulses to stimulate nerves in the body. Nerves in the human body exhibit an all or none depolarization action to electrical stimulation; that is, if the electrical stimulus input is not of sufficient intensity to reach the depolarization threshold for the time it is applied to the nerve, no nerve depolarization will result. Strength-duration, S-D, curves for nerves are a plot of stimulus intensity versus pulse duration. The curves exhibit a common hyperbolic or inverse logarithmic shape over a wide range of pulse widths. The only difference in S-D curves from one class of nerves to another is the amplitude scale. The smaller nerve requires the largest depolarizing amplitude at a given pulse width.

Pain is a subjective phenomenon. The degree of pain relief is a subjective interpretation. By the study of the post treatment behavior of pain patients, one can assess treatment quality. It has been observed that a pain patient using a transcutaneous electrical nerve stimulation device provided with variable pulse width can get pain relief to a greater degree than a similar device having a fixed setting of pulse width. Patient portable instrumentation has been used for the treatment of chronic pain. These instruments stimulate the touch fiber nerves from the skin surface. The instruments have intensity controls, such as a single amplitude control. These instruments are further classified as to wave form: alternating square waves, spike exponential waves, symmetrical square waves, and square-spike combination waves. In the square wave units, means are provided for variation of intensity, the pulse widths, and the pulse repetition rate.

SUMMARY OF INVENTION

The invention is directed to a living tissue stimulating device that has an electrical circuit provided with control means for coordinating the electrical pulse width with the stimulus intensity in a prescribed non-linear manner such that negligble subjective stimulus intensity is perceived as the pulse width is changed. The coordinated electrical pulse width and stimulus intensity follows a selected nerve strength-duration curve which has an inverse logarithmic shape. The device has pulse generator means operable to produce periodic electrical pulses. The frequency of the pulses is controlled by an adjustable first control means operably connected to the pulse generator. Means for controlling the pulse width are connected to the output of the pulse generator. The means for controlling the pulse width has an adjustable control operable to vary the pulse width. The pulse from the means controlling the pulse width is directed to second control means operable to vary the intensity of the pulse. The adjustable control and second control means are mechanically coupled so that they operate in response to each other to decrease pulse intensity when there is an increase in pulse width so that negligible subjective stimulus changes are perceived by the patient. The amplitude of intensity decreases with an increase in pulse width along a curve that follows a generally hyperbolic strength-duration curve of living tissue.

IN THE DRAWINGS

DESCRIPTION OF PREFERRED EMBODIMENT

Figure 1:
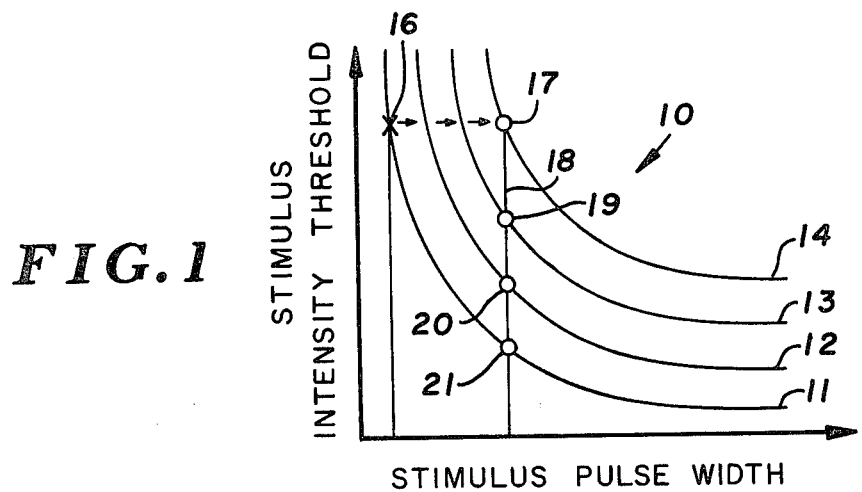
FIG. 1 is a diagram of strength-duration curves for various classes of nerve fibers, showing horizontal movement of stimulation with pulse width variations.

Referring to FIG. 1, there is shown a data graph 10 of strength-duration, S-D, curves for various classes of nerve fibers. The horizontal coordinate is a measurement of stimulus pulse width. The vertical coordinate is a measurement of stimulus intensity threshold. The curves exhibit the common hyperbolic or inverse logarithmic shape and are identified with the reference numerals 11, 12, 13, and 14. Curves 11, 12, 13, and 14 are the touch, pain, and motor nerve fibers within a nerve tract or bundle.

The initial stimulation is at point 16 on a touch nerve fiber. The pulse width is increased to point 17 without changing the amplitude of the stimulus. All nerve fiber classes below point 17 along line 18 are stimulated, as indicated by points 19, 20, and 21. By increasing the pulse width, there is now a stimulation of touch, pain, and motor nerve fibers.

It has been found that the stimulus intensity decreases across the nerve bundle inversely with distance. Thus, only part of the nerves in a bundle are activated by narrow pulse widths due to their large firing threshold. Also, a change in pulse width, if doubled, may result in a proportionately greater recruitment of nerve fibers due to the non-linear relationship between pulse width and threshold. These factors give the patient the sensation that pulse width variations also change the intensity or energy of the stimulus due to the increase in recruitment of the number of nerves within the tract or fiber.

The approximate equation describing threshold action of nerve fiber as a function of pulse width is:

$$I_s = \frac{A I_0}{\text{Log}\left(1 + \frac{T}{T_0}\right)}$$

$I_s$ = Stimulus intensity
A = Constant for each nerve fiber class
$I_0$ = Rheobase current (minimum threshold current)
T = Pulse width of stimulus
$T_0$ = Chronaxie (pulse width at two times the Rheobase value).

The S-D curves shown in FIG. 1 are in accordance with this equation.

Figure 2:
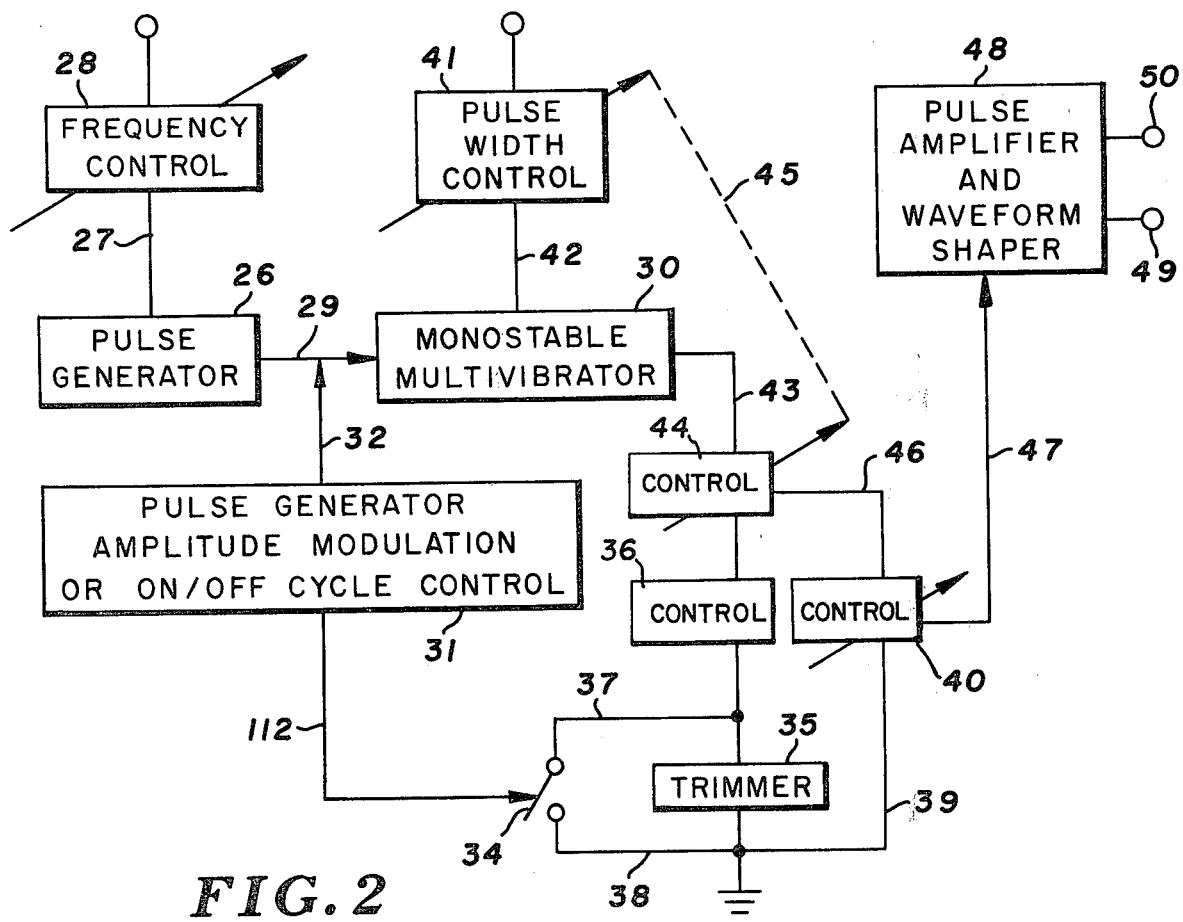
FIG. 2 is a block diagram of a tissue stimulation device which may be employed to practice the invention.

Referring to FIG. 2, there is shown a block diagram of the body stimulation device employed to practice the invention. The body stimulation device can be packaged for use as a patient worn portable external apparatus or an implantable apparatus. The invention is not intended to be limited to nerve stimulation. The device may be used for cardiac stimulation, brain stimulation, and other organ or body tissue stimulation which exhibit strength-duration stimulation characteristics. The device is also useable as a therapeutic or orthotic muscle stimulator.

A pulse generator 26 generates the basic stimulus frequency. Generator 26 is a free-running multivibrator connected with a line 27 to a frequency control potentiometer 28. Potentiometer 28 is adjustable to regulate the frequency output of pulse generator 26. The output of pulse generator 26 is connected with a line 29 to a monostable multivibrator 30. A pulse generator 31 electrically switches switch 34 via line 112. Cycled connection 32 couples generator 31 with line 29. Lines 37 and 38 connect switch 34 across a trimmer potentiometer 35. Line 39 connects potentiometer 35 with a variable control 40.

A variable pulse width control 41 is connected with line 42 to multivibrator 30 to control the pulse width of the output of multivibrator 30. Pulse width control 41 is ganged with a control 44 through mechanical linkage 45. The line 43 connects output of multivibrator 30 to control 44. A control 36 connects trimmer 35 with control 44. The circuit details of control 36 are hereinafter described. Control 44 is adjusted simultaneously with the adjustment of pulse width control 41 to vary the pulse width of the multivibrator 30 and the output intensity of the signal from control 44. This adjustment is in a prescribed non-linear manner such that the amplitude of stimulation intensity decreases with an increase in pulse width. This non-linear relationship follows a hyperbolic strength-duration curve of a nerve or living tissue. A line 46 connects control 44 with variable control or potentiometer 40.

The output of variable potentiometer 40 is carried through a line 47 to a pulse amplifier and wave form shaper 48. Amplifier shaper 48 produces a stimulus current or voltage source pulse which is transmitted via lines 49 and 50 to stimulus electrodes (not shown). The electrodes can be the electrode structures disclosed in U.S. Pat. No. 3,817,252.

Figure 3:
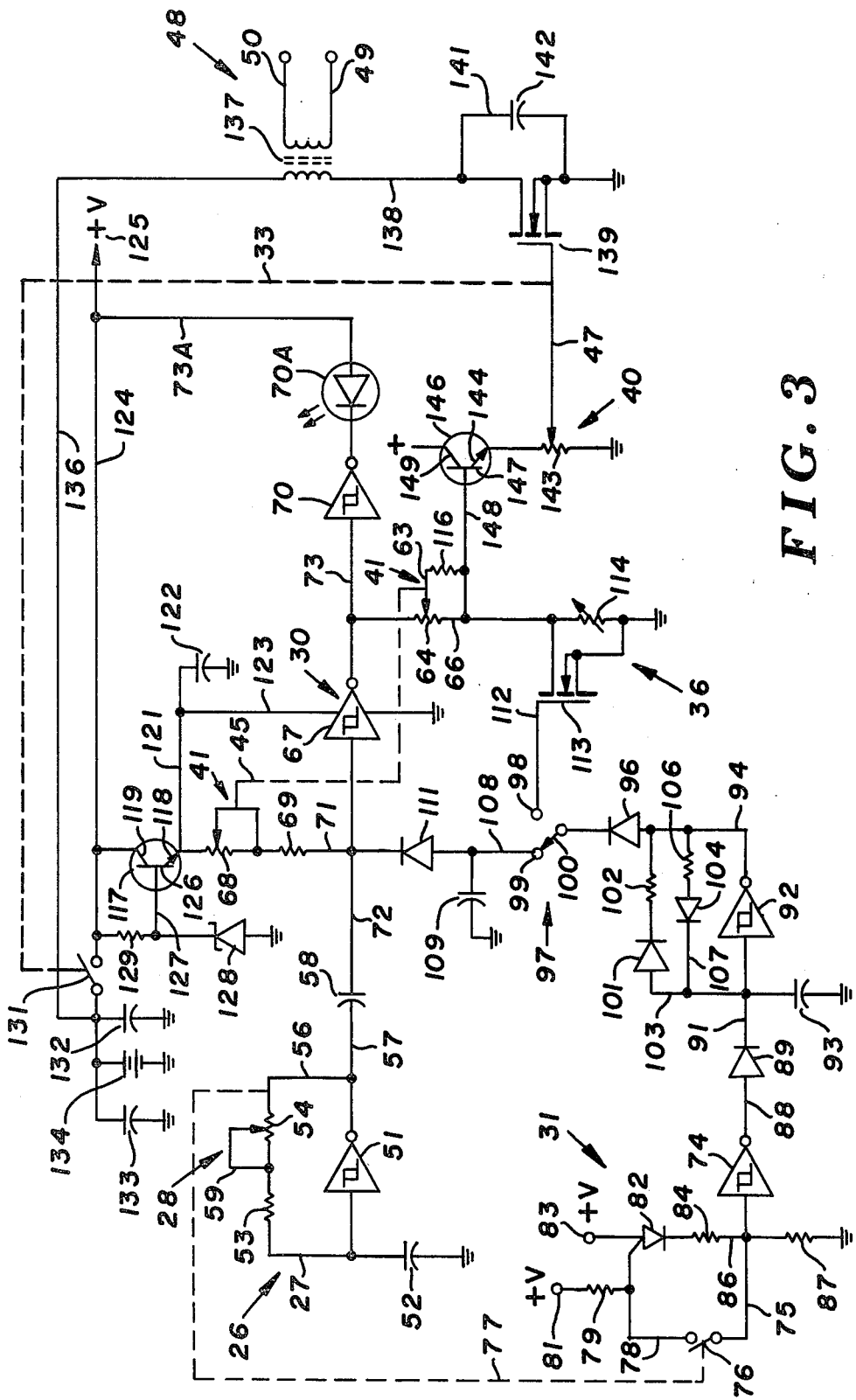
FIG. 3 is a circuit diagram of the tissue stimulation device.

Referring to FIG. 3, there is shown a schematic circuit diagram of the apparatus of the invention in accordance with the block diagram of FIG. 2. Pulse generator 26 has a logic inverter 51. Preferably, inverter 51 is one of six of a C-mos hex inverter chip on a single integrated circuit. Inverter 51 is connected to a capacitor 52 leaading to the ground and series connected resistors 53 and 54. A line 56 connects resistor 54 to a line 57 joining inverter 51 with a capacitor 58. Pulse generator 26 changes state when capacitor 52 charges through the input threshold.

Variable resistor element 68 is mechanically connected with a linkage 45 to a movable contact element 63 cooperating with resistor 64 located in a line 66 of control 41. Thus, the pulse width output of multivibrator 30 is simultaneously adjusted with the output signal intensity of control 63. The width of the pulse is controlled without a perceived increase in current amplitude. The pulse width and current amplitude is controlled in a prescribed non-linear manner such that the amplitude of stimulation intensity decreases with an increase in pulse width. This non-linear relationship follows a hyperbolic strength-duration curve of a nerve or living tissue.

Monostable vibrator 30 has a logic inverter 67 coupled to capacitor 58 and a potentiometer 68 through a resistor 69. Resistor 69 is located in a line 71 connected to a line 72 electrically joining capacitor 58 with logic inverter 67. Logic inverter 67 is connected to another logic inverter 70 with line 73. A light emitting diode 70A in line 73A connects inverter 70 to +V power at 125.

The pulse generator amplitude modulation and on-/off cycle control 31 has a first logic inverter 74 connected to a line 75 leading to a switch 76. A mechanical linkage 77 connects switch 76 to potentiometer 59. A line 78 connects switch 76 with a resistor 79 coupled to a plus voltage source 81. Line 78 is also connected to a programmable unijunction transistor (P.U.T.) 82. P.U.T. 82 is connected to a plus voltage source 83 and a resistor 84 located in line 86. Line 86 is connected to inverter 74 and includes a resistor 87 coupled to ground.

Logic inverter 74 is connected to a line 88 joined to a diode 89. A line 91 connects diode 89 with a second logic inverter 92. A capacitor 93 is coupled to line 91 and ground. Logic inverter 92 is connected with a line 94 to a diode 96 leading to a switch 97 having a first amplitude modulation contact 98 and a second cycled contact 99. A switching element 100 is operative to selectively engage contacts 98 and 99. A diode 101 and resistor 102 connected in series in line 103 is coupled to lines 91 and 94 in parallel with logic inverter 92. A second diode 104 and resistor 106 is located in line 107 joined to lines 94 and 103 in parallel with logic inverter 92.

Contact 99 of switch 97 is connected to a line 108 leading to a diode 111. Diode 111 is connected to line 72. A capacitor 109 is coupled to line 108 between contact 99 and diode 111 and ground.

Contact 98 of switch 97 is connected to a line 112 joined to a transistor 113. A variable potentiometer 114 is connected to transistor 113 and ground. Line 66 having a resistor 116 is connected to the variable potentiometer 114 to complete control 36.

A transistor 117 is connected to potentiometer 68. Transistor 117 has an emitter electrode 118 and a collector electrode 119 joined to a base electrode 126. A line 121 connects the emitter electrode 118 to potentiometer 68 and a capacitor 122 joined to ground and a line 123 leading to logic inverter 67. Collector electrode 119 is connected to line 124 joined to a positive voltage 125. Base electrode 126 is connected to a line 127 interposed between a diode 128 and a resistor 129. Resistor 129 is connected to a switch 131. Switch 131 is connected to a pair of capacitors 132 and 133 and a power supply or battery 134. A line 136 connects power source 134 to a transformer 137 having output leads 49 and 50. Transformer 137 is part of the pulse amplifier and wave form shaper 48 which also includes line 138 connected to a field effect transistor 139. A line 141 extends around field effect transistor 139 and includes a capacitor 142. Field effect transistor 139's gate control element is connected to line 47 which leads to a potentiometer 143 of control 40. Potentiometer 143 is connected to an emitter 144 of transistor 146. The base electrode 147 of transistor 146 is connected to a line 148 leading to potentiometer 64. The collector electrode 149 of transistor 146 is connected to a positive power source.

In operation, pulse generator 26 changes state when capacitor 52 charges through the input threshold. The ouput of inverter 51 then switches state and discharges capacitor 52 through the series combination of resistors 53 and 54 and the cycle repeats. Resistor 54 controls the repetition rate which can vary from 1 p.p.s. to 100 p.p.s., or any other rate range as determined by the time constant of capacitor 52 times resistors 53 plus 54. Capacitor 58, logic inverter 67, and potentiometer 68 make a one-shot multivibrator. When the output of logic inverter 51 goes low, capacitor 58 charges through resistor 68 until the switching threshold of logic inverter 67 is passed, at which time the output of logic inverter 67 goes low and stays low until the next high to low transition of logic inverter 51 output. The result is a current pulse whose width range varies between 10 and 400 micro-seconds in accordance with the values of the components of the circuit. The pulse at the output of logic inverter 67 passes through the strength-duration intensity control network of potentiometer 64, resistors 116, 114, and 143. Potentiometer 64 is ganged with potentiometer 68 with a mechanical linkage 45 such that, as the control is rotated clockwise, potentiometer 68 increases in resistance and the pulse width becomes wider. Simultaneously, potentiometer 64 connected as a voltage divider potentiometer moves clockwise and the pulse amplitude driving transistor 146 decreases in amplitude. Thus, at the full clockwise position, the pulse width is approximately 400 micro-seconds and the output is 33 percent of maximum intensity. Variation of potentiometer 64 varies the pulse width and the amplitude. A minimum pulse width and maximum amplitude is achieved when the wiper of potentiometer 41 is at its upper position. Resistor 116 loads potentiometer 64 in a manner to create curves that follow the S-D curves of FIG. 1.

Logic inverters 74 and 92 and their associated network serve to form a pulse generator circuit that either cycles the stimulator on/off or modulates the intensity of the signal. The modulations have a subjective preference quality and, thus, improve pain relief. In addition, when used in the cycled mode, the power consumption is greatly reduced. This increases battery life, which is an important factor in implantable devices.

Switch 76 allows logic inverter 74 output to go low, reverse biasing diode 89, and allows logic inverter 92 to act as a repetitive pulse generator with on to off times determined by resistor 106, capacitor 93, and resistor 102. This action is latched on by P.U.T. 82 which holds the input of logic inverter 74 high. Diodes 101 and 104 allow separation of the time constants. Diode 96 couples a high signal to either logic inverter 67 via diode 111 when switch 97 engages contact 99 or couples a high signal to transistor 113 when contact element 100 engages contact 98. When the signal goes high, transistor 113 turns on and decreases amplitude for the time the high pulse is on. If the switch engages contact 99 diode 111 clamps off triggering of monostable logic inverter 67 and the device is off for this period of time. Capacitor 109 prevents the stimulator from suddenly turning on when logic inverter 92 goes low, as it discharges through diode 111, keeping logic inverter 67 off. This provides a soft start to prevent startling the patient. The soft start time may be approximately 50 m.s.

Transistor 139 and transformer 136 amplify and shape the pulse to produce an output pulse that is a square wave constant voltage followed by an undershoot exponential that is constant current. Transistor 117 and its associated network regulates the voltage to the pulse timing and width circuits such that minimum changes occur over the normal range of use of the battery discharge curve.

While there is shown and described a preferred embodiment of the nerve stimulation circuit of the invention, it is understood that the stimulation circuit can be changed and modified and used to stimulate other living tissue, body functions, and organs. The invention is defined in the following claims.

The embodiments of the invention in which an exclusive property or privilege is claimed is defined as follows:

1. A device for electrically stimulating living tissue comprising: pulse generator means for producing periodic electrical pulses, first control means for controlling the pulse width of said periodic electrical pulses, adjustable second control means for varying the intensity of said periodic electrical pulses, and means coupling said first and second control means to simultaneously adjust said first and second control means relative to each other whereby an adjustment of the first control means causes an adjustment of the second control means to change the intensity of the periodic electrical pulses as a function of a change of the width of said pulses wherein the amplitude of stimulation intensity decreases with an increase in pulse width and the amplitude of stimulation intensity increases with a decrease in pulse width, and means for carrying said pulses to tissue engaging electrodes.

2. The device of claim 1 wherein: the first control means includes a potentiometer for controlling the pulse width of the electrical pulses.

3. The device of claim 1 including: on/off cycle control means connected to the pulse generator means for producing periodic electrical pulses for modulating the pulses from the pulse generator means.

4. The device of claim 1 wherein: the pulse generator means for producing periodic electrical pulses is connected to monostable multivibrator means, said first control means connected to the monostable multivibrator means to control the pulse width of the electrical pulses from the multivibrator means, said second control means being connected to the multivibrator means to receive output signals therefrom.

5. The device of claim 4 wherein: said means coupling said first and second control means includes mechanical means operably connecting the first and second control means.

6. The device of claim 5 wherein: said first and second control means are potentiometers, said potentiometers being operatively connected with said mechanical means.

7. The device of claim 1 wherein: the first control means includes a first variable potentiometer, said second control means includes a second variable potentiometer, and said means coupling said first and second control means including mechanical means operably connecting said first and second potentiometers.

8. The device of claim 7 wherein: said means coupling said first and second potentiometers includes a mechanical means.

9. The device of claim 1 including: adjustable means operable to control the frequency of the periodic electrical pulses produced by the means for producing said pulses.

10. The device of claim 9 wherein: the adjustable means has means operable to selectively increase or decrease the frequency of said electrical pulses, and said second control means has means operable to selectively increase or decrease the intensity of said electrical pulses, said means coupling said first and second control means being operable in response to operation of the first control means to decrease the intensity of the electrical pulses when there is an increase in the width of the electrical pulses so that negligible subjective stimulus intensity changes are perceived by the patient.

11. The device of claim 1 wherein: said means for carrying said electrical pulses includes first and second output means operatively coupled to the second control means, said output means adapted to be connected to tissue engaging electrodes.

12. The device of claim 1 wherein: the second control means includes means to change the intensity of the pulse approximately as a function of change of the pulse width of the pulse in accordance with the equation:

$$I_s = \frac{A I_0}{\text{Log}\left(1 + \frac{T}{T_0}\right)}$$

$I_s$ = Stimulus intensity
$A$ = Constant for each nerve fiber class
$I_0$ = Rheobase current (minimum threshold current)
$T$ = Pulse width of stimulus
$T_0$ = Chronaxie (pulse width at two times the Rheobase value).

13. A device for electrically stimulating living tissue of a patient comprising: first means for producing periodic electrical pulses, second means for controlling the pulse width of said periodic electrical pulses, third means for varying the intensity of said periodic electrical pulses, control means operably connected to the second and third means to simultaneously operate the second and third means to decrease the intensity of the pulses as a function of an increase in the width of said pulses and increase the intensity of the pulses as a function of a decrease in the width of said pulses so that negligible subjective stimulus intensity changes are perceived by the patient when the pulse width of the pulses is changed and means for carrying said pulses to tissue engaging electrodes.

14. The device of claim 13 wherein: the first means includes monostable multivibrator means operable to produce said electrical pulses, said control means includes first adjustable means for controlling the pulse width of the pulses produced by the monostable multivibrator means, and second adjustable means for varying the intensity of said pulses, and means coupling said first and second adjustable means whereby an adjustment of the first adjustable means causes an adjustment of the second adjustable means.

15. The device of claim 14 wherein: said first and second adjustable means each include a variable potentiometer.

16. The device of claim 14 wherein: said means coupling said first and second adjustable means include mechanical means operably connecting said first and second adjustable means.

17. The device of claim 13 wherein: said change of the intensity of the pulse is in accordance with the equation:

$$I_s = \frac{A I_0}{\text{Log}\left(1 + \frac{T}{T_0}\right)}$$

$I_s$ = Stimulus intensity
$A$ = Constant for each nerve fiber class
$I_0$ = Rheobase current (minimum threshold current)
$T$ = Pulse width of stimulus
$T_0$ = Chronaxie (pulse width at two times the Rheobase value).

18. The device of claim 13 wherein: said control means includes adjustable first control means operable to control the pulse width of the periodic electrical pulses produced by the first means, and adjustable second control means for varying the intensity of said periodic electrical pulses, and means coupling said first and second control means to adjust said control means relative to each other whereby an adjustment of the first control means causes an adjustment of the second control means to change the intensity of the pulses as a function of the change in the pulse width of said pulses.

19. The device of claim 18 wherein: said means coupling said first and second control means includes mechanical means operably connecting said first and second control means.

20. The device of claim 18 wherein: said first and second control means each include a variable potentiometer, said means coupling said first and second control means including means connecting said variable potentiometer.

21. The device of claim 13 wherein: said first means includes a pulsed generator and monostable multivibrator means connected to the pulse generator, said control means being connected to the pulse generator to control the pulse width of the electrical pulses produced thereby and connected to the output of the multivibrator means to control the pulse intensity of said pulses.

22. The device of claim 13 including: on/off cycle control means connected to the first means for modulating the pulses from the first means.

23. The device of claim 13 wherein: the control means includes amplitude modulation means.

* * * * *

UNITED STATES PATENT AND TRADEMARK OFFICE
CERTIFICATE OF CORRECTION

PATENT NO. : 4,340,063
DATED : July 20, 1982
INVENTOR(S) : Donald D. Maurer

It is certified that error appears in the above-identified patent and that said Letters Patent are hereby corrected as shown below:

Column 3, line 47, "leaading" should be -- leading --.

Column 5, line 9, "and" should be -- to --.

Column 6, line 4, "embodiments" should be -- embodiment --.

Signed and Sealed this

Twenth-eighth Day of September 1982

[SEAL]

Attest:

GERALD J. MOSSINGHOFF

Attesting Officer

Commissioner of Patents and Trademarks